(12) United States Patent
Brüning et al.

(10) Patent No.: US 6,942,871 B2
(45) Date of Patent: Sep. 13, 2005

(54) HIGHLY VISCOUS MICROEMULSIONS BASED ON SUGAR SURFACTANTS, OILY BODIES AND ALUMINIUM SALTS AND THE USE THEREOF IN THE PRODUCTION OF ANTI-PERSPIRANT GEL AND STICK PREPARATIONS

(75) Inventors: Stefan Brüning, Duesseldorf (DE); Achim Ansmann, Erkrath (DE); Susan Lang, Juelich (DE); Bernhard Guckenbiehl, Cologne (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 273 days.

(21) Appl. No.: 10/204,866

(22) PCT Filed: Jan. 31, 2001

(86) PCT No.: PCT/EP01/00986

§ 371 (c)(1),
(2), (4) Date: Dec. 16, 2002

(87) PCT Pub. No.: WO01/58417

PCT Pub. Date: Aug. 16, 2001

(65) Prior Publication Data

US 2003/0118534 A1 Jun. 26, 2003

(30) Foreign Application Priority Data

Feb. 9, 2000 (DE) .......................................... 100 05 556

(51) Int. Cl.$^7$ .............................. A61K 7/00; A61K 7/32
(52) U.S. Cl. ......................... 424/401; 424/65; 424/66; 424/67; 424/68; 424/400
(58) Field of Search .............................. 424/65, 66, 67, 424/68, 400, 401

(56) References Cited

U.S. PATENT DOCUMENTS

| | | |
|---|---|---|
| 1,985,424 A | 12/1934 | Piggott |
| 2,016,962 A | 10/1935 | Flint et al. |
| 2,703,798 A | 3/1955 | Schwartz |
| 5,374,716 A | 12/1994 | Biermann et al. |
| 5,576,425 A | 11/1996 | Hill et al. |
| 5,980,874 A | 11/1999 | Foerster et al. |

FOREIGN PATENT DOCUMENTS

| | | |
|---|---|---|
| DE | 1 165 574 | 8/1960 |
| DE | 2 024 051 | 5/1970 |
| DE | 195 14 269 | 10/1996 |
| DE | 197 56 377 | 6/1999 |
| EP | 0 291 334 | 11/1988 |
| EP | 0 301 298 | 2/1989 |
| GB | 962919 | 7/1964 |
| GB | 1 333 475 | 10/1973 |
| GB | 2 299 270 | 10/1996 |
| WO | WO 90/03977 | 4/1990 |
| WO | WO 92/06984 | 4/1992 |
| WO | WO 96/23483 | 8/1996 |

OTHER PUBLICATIONS

J. Falbe et al., Römpp Lexikon Chemie, Version 2.0, Stuttgart/New York; Georg Thieme Verlag 1999, p 5101.
C. C. Akoh et al., "Preparation of Trehalose and Sorbitol Fatty Acid Polesters by Interesterification" JAOCS, vol. 66, No. 11 (Nov. 1989) pp 1581–1587.
S. Ropuszynski et al., "Dehydration of D–Sorbitol in the Presence of Sodium Phosphates", Tenside Surf. Det.27 (1990), pp. 350–351.
M. Heike Kelkenberg, "Detergenzien auf Zuckerbasis", Tenside Surfactants Detergents 25, 1988 pp 8–13.
"Kosmetische Farbemittel" of the Farbstoffkommission der Deutschen Forschungsgemeinschaft, Verlag Chemle, Weinheim, 1984, pp 81–106.

Primary Examiner—Shelley A. Dodson
(74) Attorney, Agent, or Firm—Daniel S. Ortiz; John F. Daniels

(57) ABSTRACT

A highly-viscous microemulsion containing: (a) a sugar surfactant; (b) an oil component; and (c) an aluminium-zirconium salt, and wherein the composition is transparent and has a Brookfield viscosity of at least about 100,000 mPas.

20 Claims, No Drawings

HIGHLY VISCOUS MICROEMULSIONS BASED ON SUGAR SURFACTANTS, OILY BODIES AND ALUMINIUM SALTS AND THE USE THEREOF IN THE PRODUCTION OF ANTI-PERSPIRANT GEL AND STICK PREPARATIONS

This application is a 371 of PCT/EP01/00986 filed Jan. 31, 2001.

BACKGROUND OF THE INVENTION

This invention relates generally to cosmetic emulsions and more particularly to high-viscosity microemulsions based on sugar surfactants, oil components and aluminium-zirconium salts and to their use for the production of cosmetic gel and stick formulations.

Microemulsions are optically isotropic, thermodynamically stable systems which contain a water-insoluble oil component, emulsifiers and water. The clear or transparent appearance of microemulsions is a result of the small particle size of the dispersed emulsion droplets which, for the most part, is under 300 nm, fine-droplet microemulsions brown-red in transmitted light and a shimmering blue in reflected light occurring in the 100 to 300 nm range and optically clear microemulsions occurring in the sub-100 nm range. The droplet size of the macroemulsions is for the most part above 300 nm. By virtue of their greater stability in relation to macroemulsions, the finer distribution of the inner phase, their generally greater effectiveness and the better transdermal penetration of the active principles incorporated therein, microemulsions have acquired considerable significance in the formulation of cosmetic and pharmaceutical preparations. However, their use in water-containing cosmetic gel and stick preparations which can be found on the market as antiperspirant or deodorant products requires a high consistency. Establishing the viscosity of such a system with long-chain polymers often results in loss of the required transparency or in displacement of the thermodynamic equilibrium. Conventional thickeners, mainly polymers, leave the skin feeling sticky after application of the formulations containing them. In addition, antiperspirant or deodorant products are formulated at an acidic pH of ca. 4 and, to this end, require thickener systems that are stable in this pH range, for example polydiols in combination with dibenzylidene sorbitol.

In addition, various antiperspirant sticks based on natural or synthetic waxes in which the active substance is introduced into the wax matrix as a powder have been available on the market for many years. The disadvantage of such sticks is that they are very greasy and often leave a white residue on the skin.

The complex problem addressed by the present invention was to provide high-viscosity microemulsions which would be distinguished by transparency and high stability and which could be used as antiperspirant gel or stick formulations without the adverse sensory effects of large quantities of polymeric thickeners. Oily and aqueous solutions would lend themselves to processing in the formulation, thereby simplifying homogeneous distribution.

DESCRIPTION OF THE INVENTION

The present invention relates to high-viscosity microemulsions containing

A) sugar surfactants,
B) oil components and
C) aluminium-zirconium salts.

It has surprisingly been found that the combination of sugar surfactants, oil components and aluminium-zirconium salts leads to clear transparent microemulsions with viscosities of at least 100,000 mPas, preferably 400,000 mPas and more particularly 800,000 to 3,000,000 mPas.

Besides their stability and transparency, the formulations according to the invention have a consistency which enables them to be processed into gels or sticks. Conventional polymeric thickeners, which are attended by the disadvantage that they leave the skin feeling sticky, can be reduced or even avoided altogether. Oily and aqueous solutions can be processed in the formulation so that homogeneous distribution is simplified.

Sugar Surfactants

Sugar surfactants are surface-active substances based on carbohydrates which include, for example, sugar esters, sorbitan esters and polysorbates, alkyl oligoglucosides and fatty acid glucamides. Sugar esters are esters of mono- and oligosaccharides and—in the broader sense—of sugar alcohols with organic and inorganic acids. Industrially the most important sugar esters are the mono- and diesters of the sugars, more especially sucrose, with higher fatty acids, such as lauric, myristic, palmitic, stearic or oleic acid or with tallow fatty acids. These sugar esters have pronounced surface-active properties [cf. Römpp Lexikon Chemie—Version 2.0, Stuttgart/New York; Georg Thieme Verlag 1999]. Sorbitan esters are mono-, di- and triesters of the sorbitans with fatty acids. Sorbitan esters and their ethoxylated derivatives (polysorbates) are used as particularly environmentally safe nonionic surfactants in the cosmetics, pharmaceutical and food industries [cf. J. Am. Oil Chem. Soc. 66, 1581 (1989), Tenside Surf. Deterg. 27, 350 (1990)].

Alkyl and/or Alkenyl Oligoglycosides

Alkyl and alkenyl oligoglycosides suitable as emulsifier component are known nonionic surfactants which correspond to general formula (I):

$$R^1O\text{-}[G]_p \qquad (I)$$

where $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. EP-A1-0 301 298 and WO 90/03977 are cited as representative of the extensive literature available on this subject.

The alkyl and/or alkenyl oligoglycosides may be derived from aldoses or ketoses containing 5 or 6 carbon atoms, preferably glucose. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl group $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis.

Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl group $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Fatty acid-N-alkyl Polyhydroxyalkylamides

Fatty acid-N-alkyl polyhydroxyalkylamides are nonionic surfactants corresponding to formula (II):

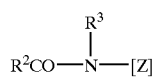

(II)

in which $R^2CO$ is an aliphatic acyl group containing 6 to 22 carbon atoms, $R^3$ is hydrogen, an alkyl or hydroxyalkyl group containing 1 to 4 carbon atoms and [Z] is a linear or branched polyhydroxyalkyl group containing 3 to 12 carbon atoms and 3 to 10 hydroxyl groups. The fatty acid-N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. No. 1,985,424, in U.S. Pat. No. 2,016,962 and in U.S. Pat. No. 2,703,798 and in International patent application WO 92/06984. An overview of this subject by H. Kelkenberg can be found in Tens. Surf. Det. 25, 8 (1988).

The fatty acid-N-alkyl polyhydroxyalkylamides are preferably derived from reducing sugars containing 5 or 6 carbon atoms, more particularly from glucose. Accordingly, the preferred fatty acid-N-alkyl polyhydroxyalkylamides are fatty acid-N-alkyl glucamides which correspond to formula (III):

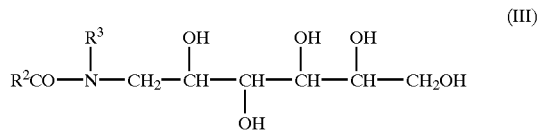

(III)

Preferred fatty acid-N-alkyl polyhydroxyalkylamides are glucamides corresponding to formula (III) in which $R^3$ is hydrogen or an alkyl group and $R^2CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid-N-alkyl glucamides (III) obtained by reductive amination of glucose with methylamine and subsequent acylation with lauric acid or $C_{12/14}$ coconut oil fatty acid or a corresponding derivative are particularly preferred. In addition, the polyhydroxyalkylamides may also be derived from maltose and palatinose.

Oil Components

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxy-carboxylic acids with linear or branched $C_{6-22}$ fatty alcohols (cf. DE 197 56 377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils (cyclomethicone, silicon methicone types, etc.) and/or aliphatic or naphthenic hydrocarbons, for example squalane, squalene or dialkyl cyclohexanes, dialkyl carbonates corresponding to formula (IV):

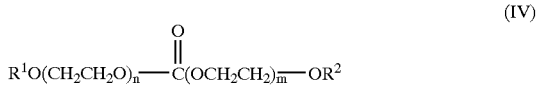

(IV)

in which $R^1$ is a linear alkyl and/or alkenyl group containing 6 to 22 carbon atoms, a 2-ethylhexyl, isotridecyl or isostearyl group or a group derived from a polyol containing 2 to 15 carbon atoms and at least two hydroxyl groups, $R^2$ has the same meaning as $R^1$ or is an alkyl group containing 1 to 5 carbon atoms and n and m independently of one another represent 0 or numbers of 1 to 100, preferably dioctyl carbonate.

Aluminium-zirconium Salts

Salts of aluminium, zirconium or zinc are used as astringent antiperspirants. Aluminium-zirconium salts in particular are distinguished by good antihydrotic activity. They are preferably complex compounds of amino acids, for example glycine, with chlorohydrate salts of the metals aluminium and zirconium in an Al:Zr ratio of 3 to 10:1 (ratio of metals to chloride 0.9 to 2.1:1). Aluminium-zirconium trichlorohydrate, aluminium-zirconium tetrachlorohydrate, aluminium-zirconium pentachlorohydrate, aluminium-zirconium octachlorohydrate are preferably used in cosmetic formulations.

Thickeners

Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride. However, the advantage of the formulation according to the invention is that the quantities of thickeners used can be reduced. If only 2% m/m thickener is added to the formulation according to the invention, an increase in viscosity of up to at least 2,000,000 mPas and preferably between 2,000,000 and 3,000,000 mPas is achieved.

Co-emulsifiers

To prepare microemulsions, sugar surfactants are used in combination with co-emulsifiers of which partial glycerides are preferably used. The ratio of sugar surfactants to partial glycerides should be in the range from 10:90 to 90:10, preferably in the range from 20:80 to 80:20 and more particularly in the range from 40:60 to 60:40.

Suitable co-emulsifiers are, for example, nonionic surfactants from at least one of the following groups:

products of the addition of 2 to 30 mol ethylene oxide and/or 0 to 5 mol propylene oxide onto linear fatty alcohols containing 8 to 22 carbon atoms, onto fatty acids containing 12 to 22 carbon atoms and onto alkylphenols containing 8 to 15 carbon atoms in the alkyl group;

$C_{12/18}$ fatty acid monoesters and diesters of products of the addition of 1 to 30 mol ethylene oxide onto glycerol;

glycerol monoesters and diesters of saturated and unsaturated fatty acids containing 6 to 22 carbon atoms and ethylene oxide adducts thereof;

products of the addition of 15 to 60 mol ethylene oxide onto castor oil and/or hydrogenated castor oil;

polyol esters and, in particular, polyglycerol esters such as, for example, polyglycerol polyricinoleate or polyglycerol poly-12-hydroxy-stearate. Mixtures of compounds from several of these classes are also suitable;

products of the addition of 2 to 15 mol ethylene oxide onto castor oil and/or hydrogenated castor oil;

partial esters based on linear, branched, unsaturated or saturated $C_{12/22}$ fatty acids, ricinoleic acid and 12-hydroxystearic acid and glycerol, polyglycerol, pentaerythritol, dipentaerythritol;

trialkyl phosphates;

wool wax alcohols;

polysiloxane/polyalkyl polyether copolymers and corresponding derivatives;

mixed esters of pentaerythritol, fatty acids, citric acid and fatty alcohol according to DE 1165574 PS and polyalkylene glycols;

mono-, di- and trialkyl phosphates and mono-, di- and/or tri-PEG-alkyl phosphates and salts thereof;

block copolymers, for example Polyethyleneglycol-30 Dipolyhydroxystearate;

polymer emulsifiers, for example Pemulen types (TR-1, TR-2) from Goodrich;

glycerol carbonate.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE 20 24 051 PS.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Typical examples of suitable polyglycerol esters are Polyglyceryl-2 Dipolyhydroxystearate (Dehymuls® PGPH), Polyglycerin-3 Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 moles of ethylene oxide.

The preparations may also contain fatty alcohols as an additional component with co-emulsifying properties. Fatty alcohols in the context of the invention are understood to be primary aliphatic alcohols, such as caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol gadolyl alcohol, behenyl alcohol, erucyl alcohol and brassidyl alcohol, and the technical mixtures thereof obtained, for example in the high-pressure hydrogenation of technical methyl esters based on fats and oils or aldehydes from Roelen's oxosynthesis and as monomer fraction in the dimerization of unsaturated fatty alcohols. Technical fatty alcohols containing 12 to 18 carbon atoms, such as coconut fatty alcohol for example, are preferred. The fatty alcohols may make up from 1 to 35% by weight and preferably from 5 to 30% by weight of the preparations.

Alternatively, diols may also be used. Typical examples are dodecane-1,12-diol, hexadecane-1,16-diol, 12-hydroxystearyl alcohol and ring opening products of epoxidized $C_{6-22}$ olefins with water or polyols, preferably glycerol. The diols may make up from 1 to 35% by weight and preferably from 5 to 30% by weight of the preparations.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, preferably methyl-quaternized difatty acid triethanolamine ester salts, being particularly preferred.

COMMERCIAL APPLICATIONS

High-viscosity microemulsions may be used in cosmetic gel and stick formulations used as antiperspirants. Antiperspirants are cosmetic formulations which reduce perspiration and hence underarm wetness by influencing the activity of the eccrine sweat glands and which contribute to a reduction of body odor. Hitherto, antiperspirants have preferably been formulated as water-free suspensions or as water-containing solutions or emulsions. Given a suitably high viscosity, however, the microemulsions according to the invention may be directly used for processing into gels or sticks. Typically they have the following composition:

A) 1–40% m/m, preferably 10–30% m/m and more particularly 15–20% m/m sugar surfactants, B) 10–50% m/m, preferably 18–35% m/m and more particularly 20–25% m/m oil components, C) 5–40% m/m, preferably 10–30% m/m and more particularly 15–20% m/m aluminium-zirconium salts, D) 0–10% m/m, preferably 1–8% m/m and more particularly 2–5% m/m thickeners, with the proviso that the quantities shown add up to 100% m/m, optionally with water and/or other typical auxiliaries and additives.

The preparations according to the invention may contain superfatting agents, fats, waxes, lecithins, phospholipids, biogenic agents, antioxidants, solubilizers, preservatives, perfume oils, dyes and the like as further auxiliaries and additives.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice germ oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs) and correspond to general formula (V):

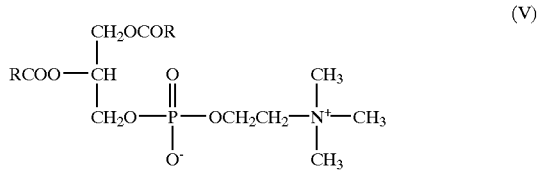

(V)

where R typically represents linear aliphatic hydrocarbon radicals containing 15 to 17 carbon atoms and up to 4 cis-double bonds. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Antioxidants

Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to μmol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers. Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Cognis GmbH, Dusseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat.

Preservatives

Suitable preservatives are, for example, phenoxyethanol, formal-dehyde solution, parabens, pentanediol or sorbic acid and the other classes of compounds listed in Appendix 6, Parts A and B of the Kosmetikverordnung (A Cosmetics Directive≡).

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the iononies, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight m/m, based on the mixture as a whole.

EXAMPLES

Microemulsions were prepared to the formulations shown in Table 1. To this end, the oil-soluble constituents were heated to 70–80° C. and melted, the water phase heated to the same temperature was partly incorporated by stirring in the oil phase together with the water-soluble constituents and the formulation was cold-stirred. The viscosity of the formulations was determined by measurement with a Brookfield RVF viscosimeter with a Helipath TF spindle at 23° C./4 r.p.m.

TABLE 1

Influence of aluminium-zirconium salt on the viscosity of microemulsions based on sugar surfactants, comparison formulation C1 and formulations 1 to 4 according to the invention; quantities of the constituents in % m/m

|  | C1 | 1 | 2 | 3 | 4 |
| --- | --- | --- | --- | --- | --- |
| INCI Name |  |  |  |  |  |
| Decyl Glucoside | 15 | 15 | 15 | 15 | 15 |
| Glyceryl Oleate | 8 | 8 | 8 | 8 | 8 |
| Dioctylcyclohexane | 11 | 11 | 7 | — | 6 |
| Cyclomethicone | 11 | 11 | 8 | 11 | 8 |
| Dioctyl carbonate | — | — | — | 11 | — |
| Dicaprylylether | — | — | 7 | — | 6 |
| Aluminium Chlorohydrate | 20 | — | — | — | — |
| Aluminium Zirconium Tetrachlorohydrex GLY | — | 20 | 20 | 20 | 20 |
| PEG-120 Methylglucosedioleate | — | — | — | — | 2 |
| Water | to 100 | to 100 | to 100 | to 100 | to 100 |
| Properties |  |  |  |  |  |
| Appearance | Clear | Clear | Clear | Clear | Clear |
| Viscosity (mPas) | 6000 | 825000 | 875000 | 850000 | 2300000 |

What is claimed is:

1. A highly-viscous microemulsion comprising:
    (a) a sugar surfactant;
    (b) an oil component; and
    an aluminium-zirconium salt, wherein the composition is transparent and has a Brookfield viscosity (RVT viscosimeter, 23° C. 4pm, TF Helipath spindle of at least about 100,000 mPas.

2. The microemulsion of claim 1 wherein the sugar surfactant is present in the composition in an amount of from about 1 to 40% by weight, based on the weight of the composition.

3. The microemulsion of claim 1 wherein the sugar surfactant is present in the composition in an amount of from about 10 to 30% by weight, based on the weight at the composition.

4. The microemulsion of claim 1 wherein the sugar surfactant is present in the composition in an amount of from about 15 to 20% by weight, based on the weight of the composition.

5. The microemulsion of claim 1 wherein the oil component is present in the composition in an amount of from about 10 to 50% by weight, based on the weight of the composition.

6. The microemulsion of claim 1 wherein the oil component is present in the composition in an amount of from about 18 to 35% by weight, based on the weight of the composition.

7. The microemulsion of claim 1 wherein the oil component is present in the composition in an amount of from about 20 to 25% by weight, based on the weight of the composition.

8. The microemulsion of claim 1 wherein the aluminium-zirconium salt is present in the composition in an amount of from about 5 to 40% by weight, based on the weight of the composition.

9. The microemulsion of claim 1 wherein the aluminium-zirconium salt is present in the composition in an amount of from about 10 to 30% by weight, based on the weight of the composition.

10. The microemulsion of claim 1 wherein the aluminium-zirconium salt is present in the composition in an amount of from about 15 to 20% by weight, based on the weight of the composition.

11. The microemulsion of claim 1 wherein the sugar surfactant is selected from the group consisting of an alkyl and/or alkenyl oligoglycoside, a fatty acid-N-alkyl polyhydroxyalkyl amide, and mixtures thereof.

12. The microemulsion of claim 1 wherein the microemulsion has a Brookfield viscosity of at least about 400,000 mPas.

13. The microemulsion of claim 1 wherein the microemulsion has a Brookfield viscosity of from about 800,000 to 3,000,000 mPas.

14. A cosmetic composition containing the microemulsion of claim 1, wherein the composition is in gel or stick form.

15. The microemulsion of claim 1 comprising:
(a) 1% to 40% by weight the sugar surfactant;
(b) 10% to 50% by weight the oil component;
(c) 5% to 40% by weight of the aluminium-zirconium salt;
(d) 0 to 10% by weight of a thickener;
(e) water; and,
(f) optionally auxiliaries, co-emulsifiers and additives; wherein, quantities of components add up to 100%.

16. The microemulsion of claim 15 comprising:
(a) 10% to 30% by weight of the sugar surfactant;
(b) 10% to 30% by weight of the oil component;
(c) 10% to 30% by weight of the aluminium-zirconium salt;
(d) 1% to 8% by weight of the thickener;
(e) water; and
(f) optionally auxiliaries, co-emulsifiers, and additives.

17. The composition of claim 15 comprising:
(a) 15% to 20% by weight of the sugar surfactant;
(b) 15% to 20% by weight of the oil component;
(c) 15% to 20% by weight of the aluminium-zirconium salt;
(d) 2% to 5% by weight of the thickener;
(a) water; and
(f) optionally auxillaries, co-emulsifiers, and additives.

18. The microemulsion of claim 1 wherein the aluminium-zirconium salt comprises a complex of amino acids with chlorohydrate salts of aluminium and zirconium in an Al:Zr atomic ratio of from 3:1 to 10:1 and a total metal to chlorine atomic ratio of from 0.9:1 to 2.1:1.

19. The microemulsion of claim 1 wherein the aluminium-zirconium salt comprises at least one member selected from the group consisting of aluminium-zirconium trichlorohydrate, aluminium-zirconium tetrachlorohydrate, aluminium-zirconium pentachlorohydrate and aluminium-zirconium octachlorohydrate and complex compounds of these salts.

20. The microemulsion of claim 18 comprising a partial glyceride co-emulsifier in a ratio of by weight of sugar surfactant to partial glyceride co-emulsifier of from 10:90 to 90:10.

* * * * *